(12) United States Patent
Sato et al.

(10) Patent No.: US 6,608,213 B1
(45) Date of Patent: Aug. 19, 2003

(54) FLUORESCENCE-LABELED PROBE FOR DNA AND A FLUORESCENCE-LABELED PLASMID

(75) Inventors: Toshinori Sato, Yokohama (JP); Yoshio Okahata, Kawasaki (JP)

(73) Assignee: Tokyo Institute of Technology, Tokyo (JP)

( * ) Notice: Subject to any disclaimer, the term of this patent is extended or adjusted under 35 U.S.C. 154(b) by 0 days.

(21) Appl. No.: 09/814,218

(22) Filed: Mar. 22, 2001

(30) Foreign Application Priority Data

Apr. 3, 2000  (JP) ........................ 2000-100898

(51) Int. Cl.[7] ................... C07D 311/78; C07D 311/88; C07D 317/08; C07H 21/02; C07H 21/04
(52) U.S. Cl. .................. 549/224; 549/227; 549/229; 536/23.1; 536/24.3; 536/24.31; 536/25.3; 536/26.6
(58) Field of Search ............... 536/23.1, 26.3, 536/24.33, 25.3, 26.6; 549/224, 227, 229

(56) References Cited

U.S. PATENT DOCUMENTS 5,846,737 A   12/1998  Kang
5,861,287 A   1/1999   Metzker et al.

OTHER PUBLICATIONS

Neves et al. Bioconjugate Chemistry 2000, vol. 11, pp. 51–55.*
Gourdie et al. Journal of Medicinal Chemistry, 1991, vol. 34, pp. 240–248.*

\* cited by examiner

*Primary Examiner*—Jezia Riley
(74) *Attorney, Agent, or Firm*—Burns, Doane, Swecker & Mathis, LLP

(57) ABSTRACT

This invention provides a precursor compound of a novel fluorescence-labeled probe for DNA, prepared by covalent binding of a fluorescent substance such as fluorescein isothiocyanate, wherein a conjugating group was bounded, with aminoalkylate phenylamine. This invention also provides a novel fluorescence-labeled probe for DNA by diazotizing amino group of phenylamine contained in the precursor compound. Furthermore, a fluorescence labeled plasmid can be produced by conjugating the fluorescence-labeled probe and purine ring of guanine contained in the DNA plasmid through diazonium group.

12 Claims, 9 Drawing Sheets

(1 of 9 Drawing Sheet(s) Filed in Color)

FLUORESCENCE-LABELED PROBE FOR DNA AND A FLUORESCENCE-LABELED PLASMID

BACKGROUND OF THE INVENTION

1. Field of the Invention

The present invention relates to a precursor of fluorescence-labeled probe, a fluorescence-labeled probe, a fluorescence-labeled plasmid, a DNA strand labeled by said fluorescence-labeled probe, and a method of preparing said fluorescence-labeled plasmid.

2. Description of Related Art

In the fields of gene therapies and genetic researches, it is very important to estimate die amount of gene introduced into a cell and to observe intracellular localization of the gene. To attain such a purpose, it is very important to visualize a DNA by labeling die DNA, using a fluorescence-labeled probe. Concerning a linear DNA strand, a method of labeling 5'-end of the linear DNA strand has been known as a method for producing a fluorescence-labeled probe to be used for the purpose described above. However, regarding a circular DNA strand, above described method can not be applied, as there is no 5'-end in the circular DNA strand. The method applied for the circular DNA strand typically utilizes an optical reaction. The method comprises the steps of introducing a fluorescence-labeled probe containing an azide group into the circular DNA strand and cleaving the circular DNA strand at aldehyde group of ribose in the DNA by irradiation of UV rays.

SUMMARY OF THE INVENTION

The conventional method using optical reaction described above requires strict reaction conditions, so that the method might be harmful for die function of the target gene. Therefore, a novel fluorescence-labeled probe capable of labeling a circular DNA strand, such as a DNA plasmid generally used in the gene therapy, achieved by a simple method under a mild condition have been desired.

Therefore, the inventors have produced a precursor compound of a novel fluorescence-labeled probe for DNA by covalent binding of a fluorescence substance, such as fluorescein isothiocyanate (FITC), wherein a conjugating group is bounded, with an aminoalkylated phenylamine. Then, amino group of phenylamine contained in said precursor was converted to diazonium salt to produce a novel fluorescence-labeled probe for DNA. Moreover, a fluorescence labeled plasmid was produced by conjugating said fluorescence-labeled probe and purine ring of guanine contained in the DNA plasmid through said diazonium group. By using the fluorescence-labeled probe for DNA according to this invention, a fluorescence-labeled DNA can be produced without deteriorating the functions of the gene. Moreover, the present invention enabled observation of gene uptake using a flowcytometer or a fluorescence microscope.

This invention is a precursor compound of a fluorescence-labeled probe for a DNA, comprising:

a residue of a fluorescence substance containing a hydrogen atom wherein said hydrogen atom is removed from said fluorescence substance;

a conjugating group that binds to said residue;

an alkylamino group having an alkyl group and amino group, said amino group being bonded to said conjugating group and said alkyl group being a linear or branched alkyl group having 1 to 16 carbon atoms; and a phenylamine having phenyl group and amino group, said alkyl group being bonded to said phenyl group at the para-position of said phenyl group.

The structure of a typical precursor of DNA probe according to the present invention is illustrated in FIG. 1, comprising fluorescein isothiocyanate (FITC) coupled to aminophenyl ethylamine. In FIG. 1, residue of fluorescein, thioamide group, ethylamine group and aminophenyl group are indicated by (1), (2), (3) and (4), respectively. Here, said fluorescein, said thioamide group and said ethylamine group correspond to said fluorescence substance, said conjugating group and said alkylamino group described above, respectively.

The alkyl group may include a linear or branched alkyl group having 1 to 16 carbon atoms, preferably having 2 to 10 carbon atoms, more preferably in having 2 to 6 carbon atoms.

The conjugating group to be used in the present invention may include any functional group, so far as it is capable of reacting to amino group. The preferable conjugating group may include thioamide group, sulfonyl group and carbonyl group.

The fluorescence substance to be used in the present invention may include any substance so far as it is capable of emitting fluorescence and binding to said conjugating group. The preferable fluorescence substance may include fluoroscein, sulforhodamine, rhodamine, dansyl chloride and 7-chloro-4-nitrobenzoxyazole.

Furthermore, this invention is a fluorescence-labeled probe for a DNA, comprising:

a residue of a fluorescence substance containing a hydrogen atom wherein said hydrogen atom is removed from said fluorescence substance;

a conjugating group that binds to said residue; an alkylamino group having an alkyl group and amino group, said amino group being bonded to said conjugating group and said alkyl group being a linear or branched alkyl group having 1 to 16 carbon atoms; and a phenyldiazonium group having phenyl group and diazonium group, said alkyl group being bonded to said phenyl group at the para-position of said phenyl group.

The structure of a typical DNA probe according to the present invention is illustrated in FIG. 2, comprising fluorescein isothiocyanate (FITC) coupled to ethylamine phenyl diazonium group. In FIG. 2, residue of fluorescein, thioamide group, ethylamine group and phenyl diazonium group are indicated by (5), (6), (7) and (8), respectively. Here, said fluorescein, said thioamide group and said ethylamine group correspond to said fluorescence substance, said conjugating group and said alkylamino group described above, respectively.

The alkyl group may include a linear or branched alkyl group having 1 to 16 carbon atoms, preferably having 2 to 10 carbon atoms, more preferably in having 2 to 6 carbon atoms.

Furthermore, this invention is a plasmid labeled by the fluorescence probe described above. The fluorescence labeled plasmid can be prepared by ligating said fluorescence probe with a plasmid through purine ring of guanine contained in DNA of said plasmid. The method for preparing such fluorescence labeled plasmid is included within the scope of the present invention.

The method for preparing the fluorescence labeled probe according to the present invention is shown in FIG. 3. The reference numerals of chemical compounds described below correspond to the reference numerals shown in FIG. 3. As shown in FIG. 3, an active group of a fluorescence substance (compound 1), such as FITC, and amino group of an aminoalkylated phenylamine derivative (compound 2), such as aminophenyl ethylamine, are reacted. Consequently, a fluorescence compound (compound 3), containing a phenylamino group at its terminal, can be obtained. A fluorescence diazo compound (compound 4) can be obtained by diazotizing amino group of said terminal phenyl amino group of the chemical compound 3 using $NaNO_2$. When the chemical compound 4 is reacted with a DNA plasmid, the compound 4 binds to a purine ring of guanine contained in the DNA plasmid, as the terminal of chemical compound 4 being a diazonium: salt.

That is, this invention is a method for preparing a fluorescence-labeled plasmid, comprising the steps of:

preparing said fluorescence-labeled probe described above;

preparing a plasmid; and binding said phenyldiazonium group contained in said fluorescence-labeled probe with said plasmid through purine ring of guanine, said guanine being contained in DNA of said plasmid.

Moreover, this invention is a method for preparing a fluorescence-labeled plasmid according to the method described above wherein said fluorescence substance is selected from a group consisting of fluoroscein, sulforhodamine, rhodamine, dansyl chloride and 7-chloro-4-nitrobenzoxyazole.

Furthermore, this invention is a method for preparing a fluorescence-labeled plasmid according to the method described above wherein said conjugating group is selected from a group consisting of thioamide group, sulfonyl group and carbonyl group.

The FITC-labeled plasmid can be obtained by the process described above. The method for preparing FITC-labeled plasmid according to the present invention has the advantage that the reaction conditions are mild. Therefore, a fluorescence label of the target gene can be performed without deteriorating the functions of the gene.

The present invention will now be described in detail with reference to the accompanying drawings. An example of production of FITC-labeled plasmid in accordance with the present invention will be described below. However, the scope of the present invention is not to be restricted by the following embodiment.

BRIEF DESCRIPTION OF THE DRAWINGS

The patent or application file contains at least one drawing executed in color.

DETAILED DESCRIPTION OF PREFERRED EMBODIMENTS

Preparation of FITC-labeled Plasmid

Figure 1:
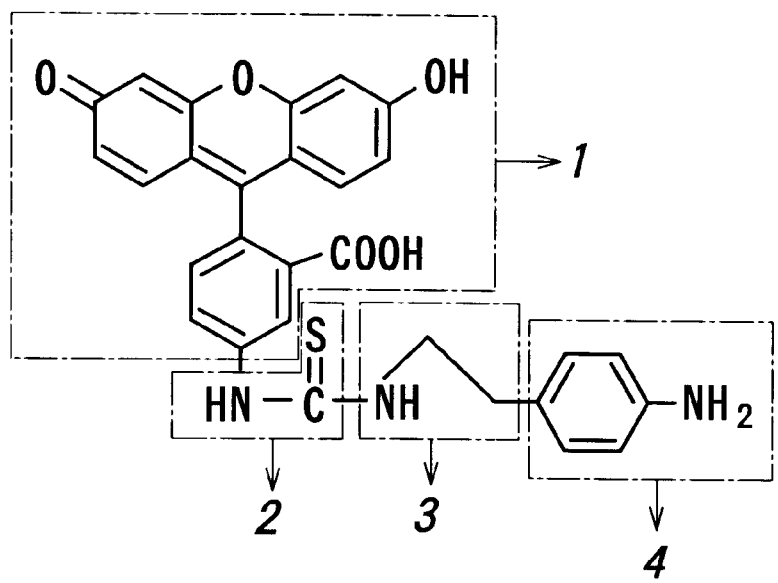
FIG. 1 is chemical formula of the fluorescence-labeled probe precursor of the present invention, wherein aminophenyl ethylamine is bound to FITC.
Figure 2:
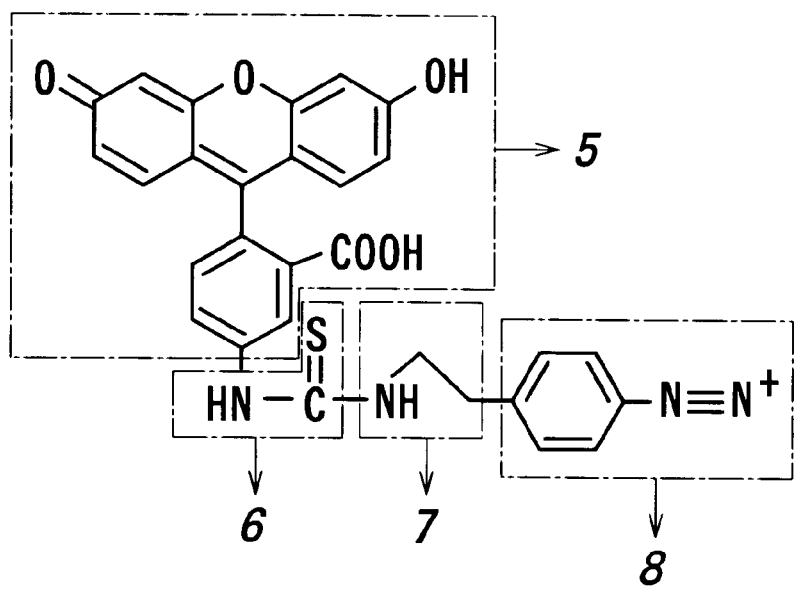
FIG. 2 is chemical formula of the fluorescence-labeled probe of the present invention, wherein aminophenyl ethyl diazonium salt is bound to FITC.
Figure 3:
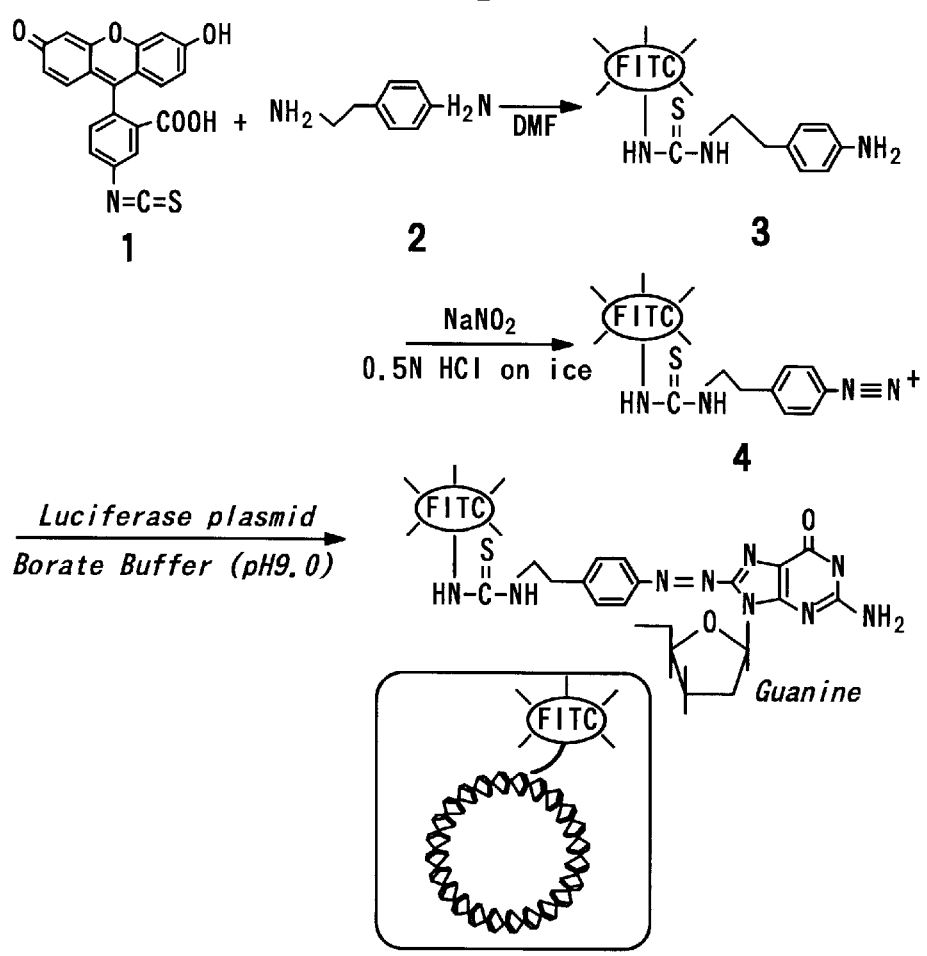
FIG. 3 is a schematic diagram that illustrates a method of preparing a FITC-labeled plasmid in accordance with the present invention.

At first, an equimolar reaction was performed. That is, 35.0 mg of 2-(4-aminophenyl)-ethylamine) (0.257 mmol, purchased from Aldrich Chemical Companies, Inc. compound 2) and 100 mg of FITC (Type-I) (compound 1) (0.257 mmol, purchased from Dojindo Molecular Technologies, Inc.) were dissolved into 1 ml of dehydrated N,N-dimethylformamide (DMF) and then stirred overnight at room temperature. The reaction proceeded in the mixture was confirmed by thin layer chromatography (TLC, hexane: ethylacetate=2:8). The analysis of the resulting compound was carried out by means of nuclear magnetic resonance (NMR)(Varian, 300 MHz), TOF-Mass spectrometry (Voyger-DE, manufactured by Perspective Bio Systems Co., Ltd.), and infrared spectrophotometer (IR) (JIR-7000, manufactured by Nippon Denshi Co., Ltd.). Subsequently, 1 ml of $NaNO_2$ solution (7.7 mg/ml) was added to 1 ml of 1N HCl, followed by addition of 150 μl of DMF solution (20.25 mg, 0.0386 mmol) containing p-aminophenylated FITC compound (compound 3) obtained by the above reaction. Consequently, a diazotized compound was obtained (compound 4).

Then, luciferase plasmid (5 mg) was dissolved into 20 ml of 0.1 M borate buffer (pH 8.4) and the diazotized compound (compound 4) was dropped into the solution. The pH of the reacting mixture was adjusted to 9.0 and the pH was maintained by NaOH. The salt concentration of the reacting mixture was adjusted to 1 M by addition of 1.18 g of NaCl. Subsequently, 50 ml of cold ethanol was added in the reaction mixture to form precipitate. The step was repeated four times to wash the precipitate. The washed precipitate was dissolved in 0.01 M Tris-HCl buffer (salt concentration 0.1 M, pH 7.4) and purified using Sepharose 4B column (fractionated molecular weight of 0.2 to 2 MDa, column diameter of 5 cm and column length of 19 cm, purchased from Amersham Pharmacia Biotech Co., Ltd.). The analysis was performed using UV (UV-2400P, manufactured by Shimazu Co., Ltd.), fluorescence (RT-540, manufactured by Shimazu Co., Ltd.) and GPC column (Sepharose 4B column), and agarose gel electrophoresis (Mupid, manufactured by Cosmo Bio Co., Ltd.). As the control experiment, mixture of die fluorescence compound (compound 3) and the plasmid was prepared by the same procedure described above except that the chemical compound 3 was not diatized. Then, an elution curve of the mixture was assayed. Consequently, 3.63 mg of yield and 72.6% of recovery were attained.

TLC Analysis

Figure 4:
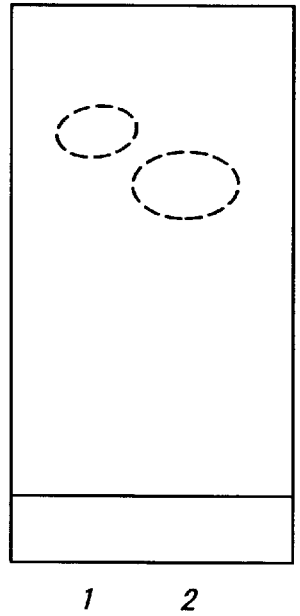
FIG. 4 is a schematic diagram that illustrates a TLC plates on which the results of the TLC analysis on p-aminophenylated FITC compound.

FIG. 4 shows the result of TLC analysis of FITC (type-I) (compound 1) and p-aminophenylated FITC compound (compound 3). In this figure, lane No. 1 corresponds to FITC (type-I) and lane No. 2 corresponds to p-aminophenylated FITC compound. The purity of FITC (type-I) (Chemical compound 1) was 90% or over and impurities were found in its row material. It was assumed that all of the row material was reacted, because a peak corresponds to the row material disappeared after the is equimolar reaction. Regarding aminophenyl ethylamine (Chemical compound 2)(Rf=0.1), which is another row material, a peak corresponds to it was not observed after the equimolar reaction.

IR Analysis

Figure 5:
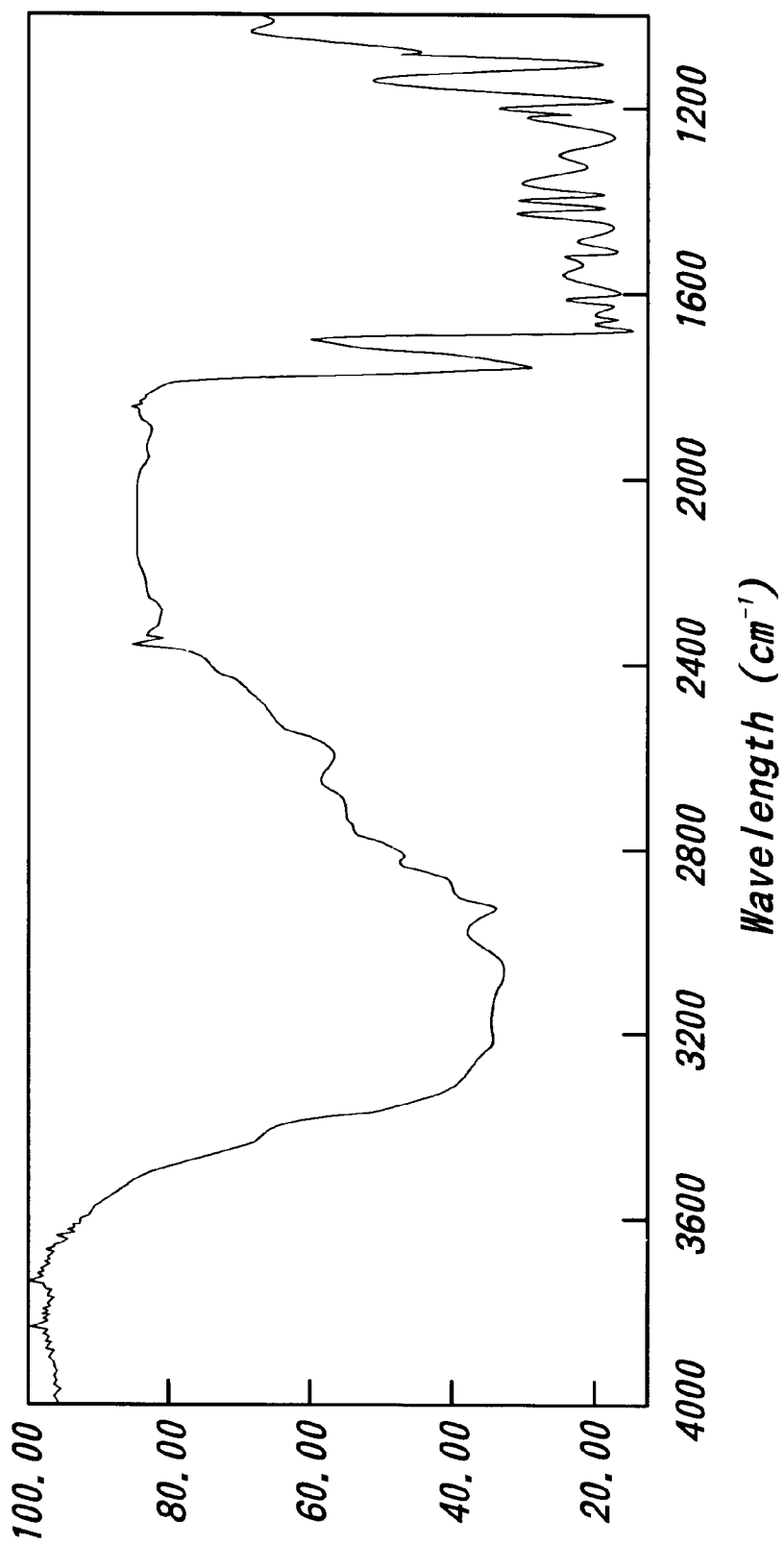
FIG. 5 is an IR chart of p-aminophenylated FITC compound.

FIG. 5 shows result of IR analysis of p-aminophenylated FITC compound (compound 2) using cast method. For the result of type-I FITC (compound 1), a stretching vibration of NCS bonding of isothiocyanate was observed at a wavelength of 2,021 $cm^{-1}$. For the result of p-aminophenylated FITC compound (compound 3) shown in FIG. 5, on the other hand, any stretching vibration of NCS bond was not observed but a stretching vibration of C=S was observed at a wavelength of 1,794 $cm^{-1}$. Accordingly, it was assumed that NCS of isothiocyanate reacted perfectly.

TOF-mass Analysis

Figure 6:
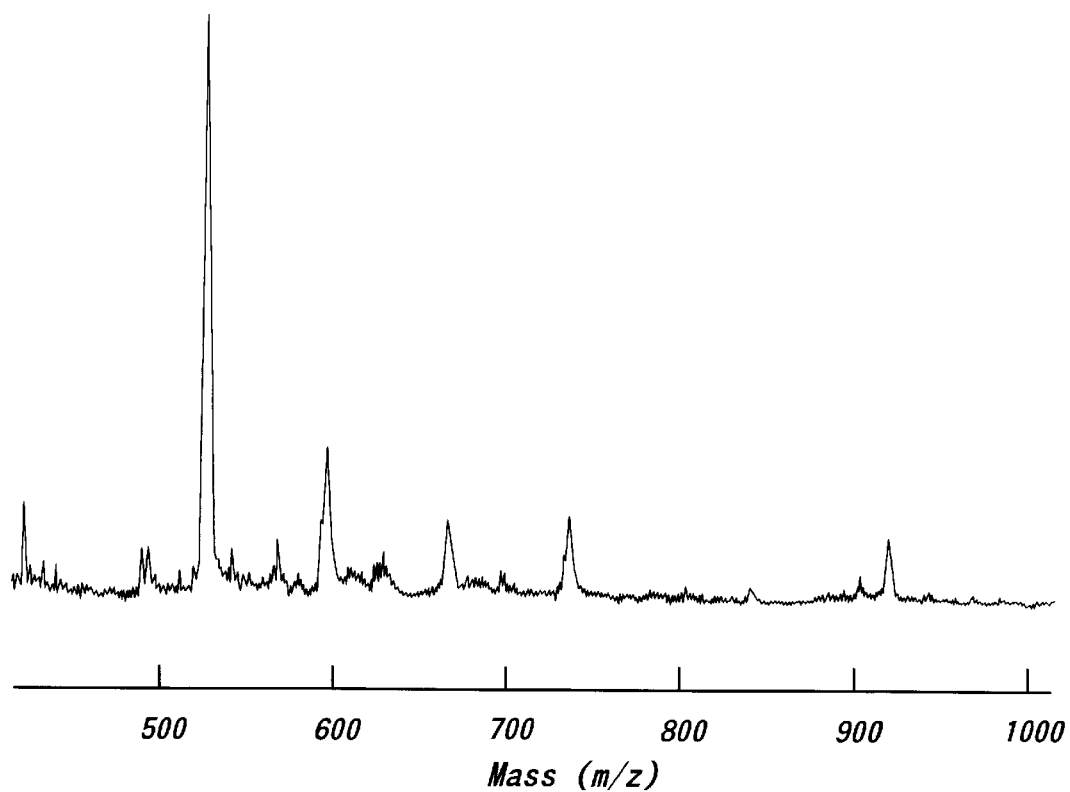
FIG. 6 is a Mass analysis chart of p-aminophenylated FITC compound.

FIG. 6 shows the results of the MALDI-TOF Mass analysis performed on p-aminophenylated FITC compound (compound 3). The measurement was performed by positive mode and CHCA was used as a matrix. For the measurement, 100 nmol of the matrix and 20 pmol of the sample were developed. The sample was dissolved in solution containing THF and $H_2O$ at the ratio of 1:1. As shown in the figure, a peak was detected at a molecular weight of 526.2031. The molecular weight of the synthetic compound of the object was 525.20. Therefore, the compound was detected at the molecular weight of 526.20 accompanied by addition of one proton. From careful consideration of the above four data, it was assumed that the objective compound was synthesized.

Gel Chromatography Analysis

The plasmid modified by FITC-fluorescence was subjected to purification procedure using Sepharose 4B column (purchased from Amersham Pharmacia Biotech Co., Ltd.) and elution curve at the purification was obtained by measuring UV and fluorescence of the eluate. In this purification, 0.01 M Tris-HCl buffer (salt concentration 0.1 M, pH 7.4) was used as eluting solution.

Figure 7:
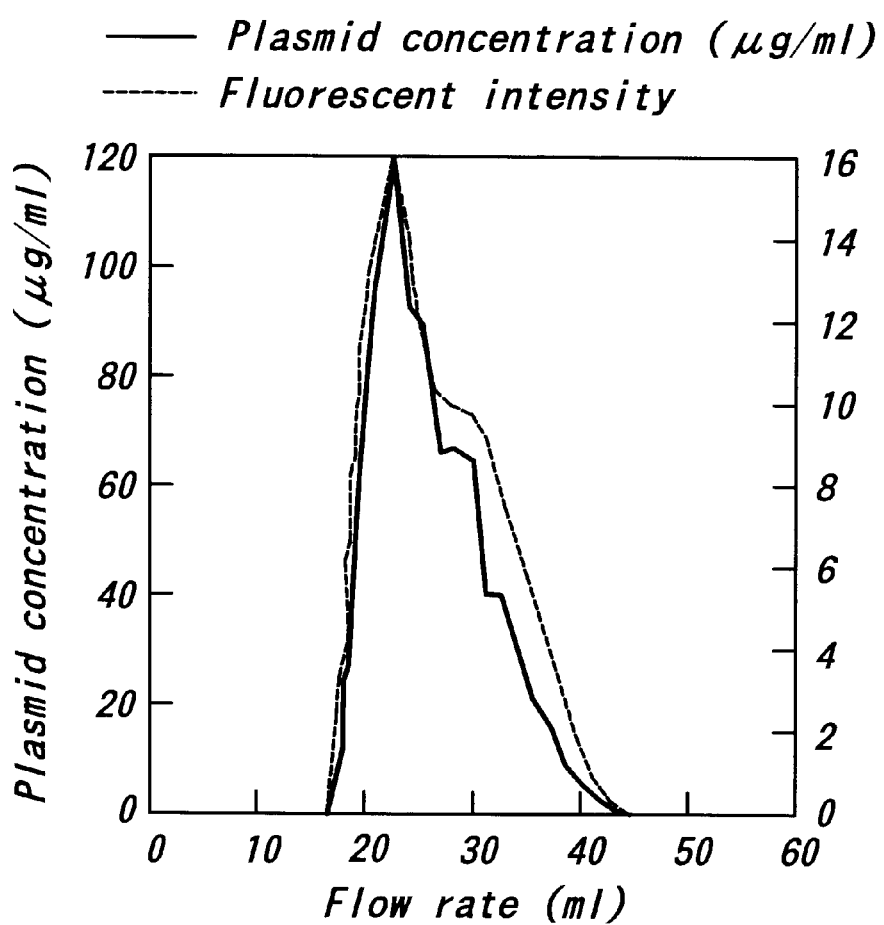
FIG. 7 is a graph that shows an elution curve of FITC-labeled plasmid obtained by eluting through a Sepharose 4B column.

FIG. 7 shows result of UV and fluorescence measured on reactant obtained by reacting the diazotized FITC (compound 4) and the plasmid. In FIG. 7, the measurement was performed at an excitation wavelength of 495 nm and a fluorescent wavelength of 520 nm. Concerning the FITC-labeled plasmid, as shown in FIG. 7, both elution curves of UV and fluorescence coincided well each other. On the other hand, concerning non-diazotized FITC, fluorescent absorption in the plasmid fraction was not observed. It means that the fluorescent reagent bonded to the plasmid by covalent binding and the fluorescent reagent did not intercalate into the plasmid. Therefore, it was assumed from the results that 1.2 molecular of FITC was introduced into one plasmid in the average.

Agarose Gel Electrophoresis Analysis

The FITC-labeled plasmid and an plasmid without any modification (not labeled) were subjected to electrophoresis using 1% agarose gel.

Figure 8:
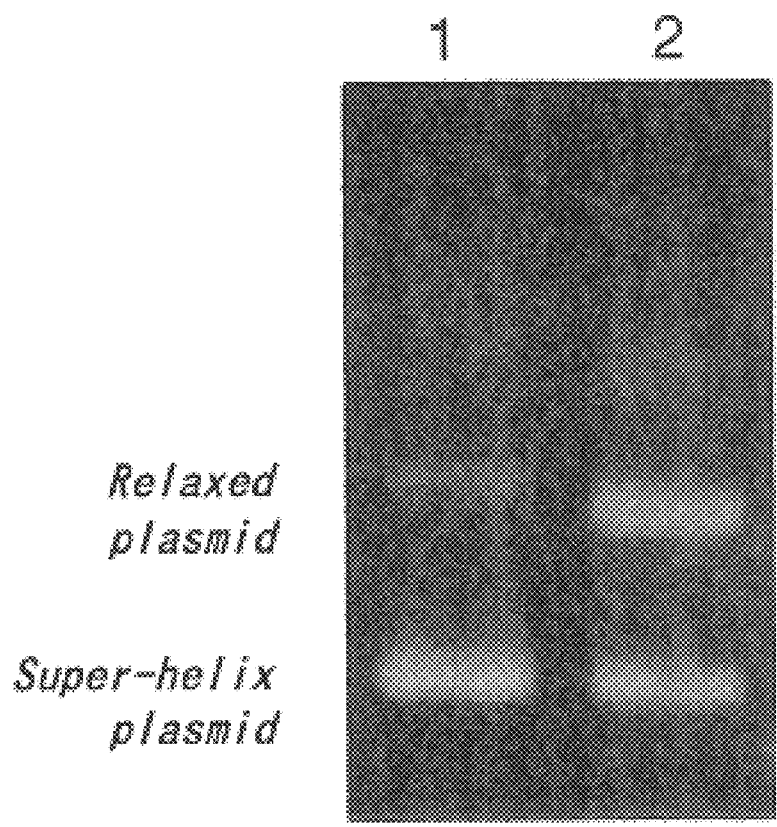
FIG. 8 is a photograph that shows the results of agarose gel electro-phoresis performed on both non-labeled plasmid and FITC-labeled plasmid.

The result is shown in FIG. 8. In this figure, lane 1 corresponds to non-labeled plasmid and lane 2 corresponds to FITC-labeled plasmid. As the result, a band corresponding to the position of control luciferase plasmid was detected on FITC-labeled plasmid of lane 2. In addition, it was revealed that the structure of super helix was maintained. It was assumed that the structure of plasmid was maintained because the amount of FITC bonded to one of plasmid was not so large (i.e., 1.2 FITCs per one plasmid).

The fluorescence-labeled plasmid of the present invention allows flow-cytometric analysis on intracellular uptake of a gene or the confocal laser microscopic analysis of intracellular localization of a gene. Heretofore, a plasmid expressing gene could not be used for such purpose, so that a linear DNA or an oligonucleotide has been used as a model compound. Therefore, is was impossible to make precise evaluation because the difference on tie uptake or localization of the gene due to the structural difference of DNA can not be neglected. The probe of the present invention resolves such problem.

Expression of Luciferase Activity in the FITC-labeled Plasmid

Transfection was performed using commercial available lipofectin utilized for gene transfer (Gibco BRL). A certain amount of plasmid (1 mg/ml in aqueous solution) and a certain amount of lipofectin (1 mg/ml) were added into ASF-104 medium (1/10 volume of medium used for transfection) adjusted to pH 6.5 and 37° C. The solution was incubated for 20 minutes to obtain complex of plasmid/lipofectin.

The expression activity of the luciferase plasmid was measured according to the conventional method. Five or $10 \times 10^4$ cells were dispensed into each well of a plate having 24-wells and cultured for 19 to 24 hours prior to transfection. After cultivation, solution of said complex at a certain concentration was inoculated into culture medium of pH 7.0 and incubated for 4 hours. Here, volume of the culture medium was ninefold of the complex solution. Then, the culture medium containing the complex was removed and washed once with serum medium. The medium was replaced with fresh serum medium (pH 7.0) and then cultured for 24 hours for transfection. After cultivation, supernatant was removed and washed three times with PBS buffer ($Ca^{2+}$ and $Mg^{2+}$ free), followed by addition of 100 μl of lysis solution (luciferase assay system, Promega Corporation). The cells were harvested by Rubber policeman and collected into Eppendorf tube. The cells collected into the Eppendorf tube were centrifuged at 10,000 rpm for 10 seconds and supernatant was obtained as cell-extraction solution. An aliquot (40 μl) of the cell-extraction solution was added into a tube for measurement. A hundred μl of substrate (luciferin) solution was also added into the tube and tapped gently by a pipette. Immediately, the mixture was subjected to measurement using a luminometer (TD-20/20 luminometer, manufactured by Promega Corporation).

Figure 9:
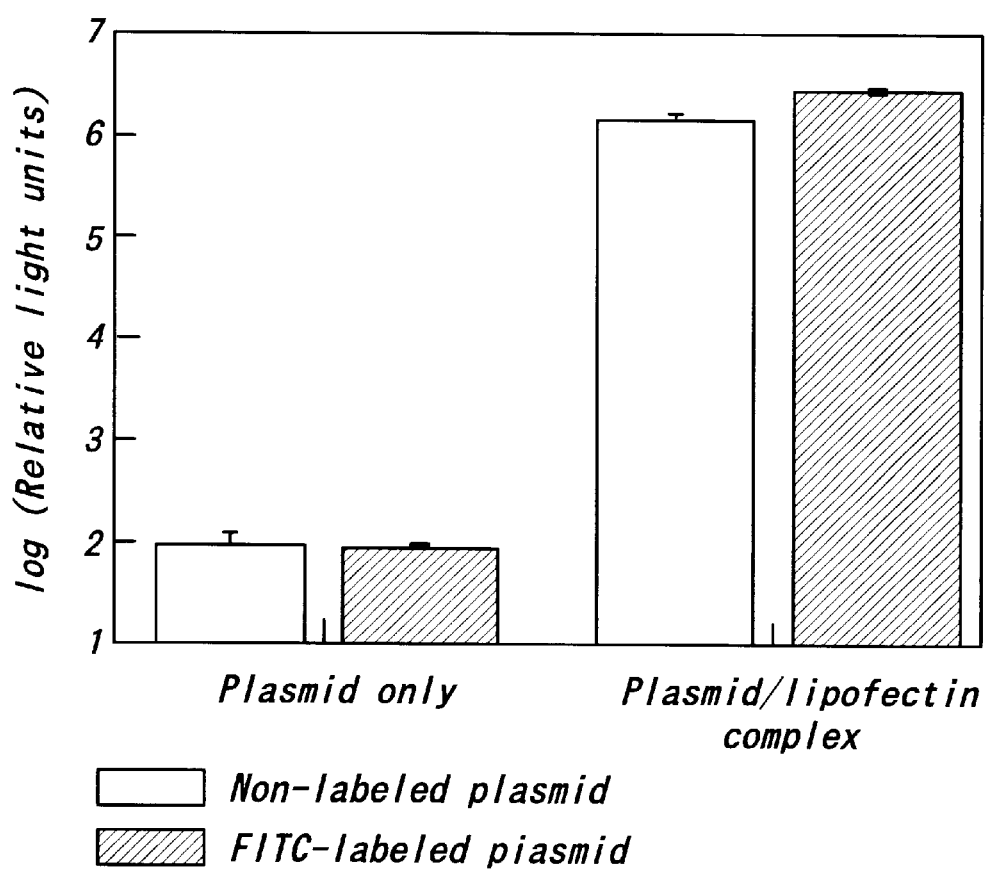
FIG. 9 is a graph that shows the luciferase expression activities of both non-labeled plasmid and FITC-labeled plasmid.

The results obtained using HeLa cells were shown in FIG. 9. The vertical axis of the graph exhibits expression activity of the plasmids, indicated as logarithmic value of relative activity. In this figure, tile expression activity observed on HeLa cells transfected by plasmid alone was represented to be 100. The error bars indicate standard deviations evaluated from twice to four times of independent experiments. In FIG. 9, furthermore, hollow columns indicate the results of non-labeled plasmid and shaded columns indicate the results of FITC-labeled plasmid. HeLa cells were transfected with plasmid alone or mixture of plasmid/lipofectin (at the ratio of 1:2.5, for 10 μg/ml of plasmid) in serum-free medium (ASF-104, purchased from Ajinomoto Co., Ltd.). In this figure, the results of HeLa cells transfected by plasmid alone were shown in the left side of the graph, while those transfected by the mixture of plasmid/lipofectin were shown in the right of the graph. As the result, FITC labeling did not cause reduction of expression activity on HeLa cells transfected by plasmid/lipofectin complex.

Measurement of Intracellular Uptake

Preparation of the plasmid/lipofectin complex and incubation of HeLa cells with the complex were performed as described in the measurement of expression activity of luciferase. The cells were prepared as follows. After HeLa cells were incubated with the complex, supernatant was removed and precipitate obtained was washed three times with PBS buffer. The cells were detached by treatment with 0.5 ml of PBS buffer containing 0.05% trypsin and 0.02% EDTA-4Na, followed by dilution with 1.0 ml of PBS buffer to obtain cell suspension. The resulting cell suspension was subjected to analysis using flow cytometry.

Figure 10:
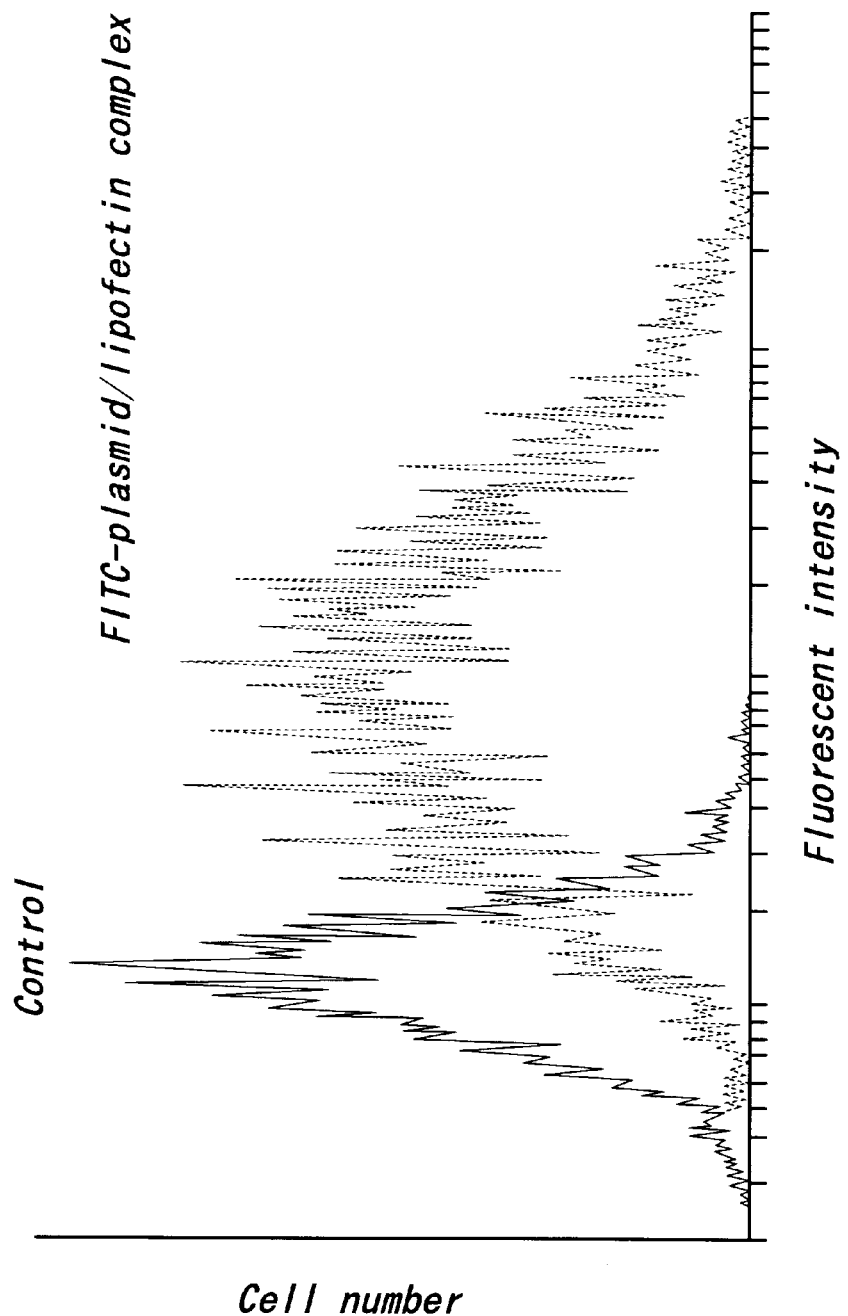
FIG. 10 is a chart obtained by a flow cytometory for the study of intracellular uptake of FITC-labeled plasmid.

The experiment was performed using HeLa cells. The results were shown in FIG. 10. HeLa cells were incubated for 2 hours with the plasmid/lipofectin complex in Eagle's minimum essential medium (MEM) containing 10% fetal bovine serum (FBS). In this medium, concentration of plasmid was 10 μg/ml and die ratio of plasmid: lipofectin was 1:2.5 in weights. As the result, flow cytometric pattern of the cells, incubated with the plasmid/lipofectin complex, shifted to higher intensity compared with the control cells. It means that fluorescent intensity of the fluorescence-labeled plasmid is sufficient for detection using flow cytometory.

Intracellular Localization Observed by Confocal Laser Scanning Microscope

Cells were prepared as follows. That is, $5\times10^4$ cells were dispensed into 35 mm of glass bottom dish (manufactured by MatTek Co., Ltd.) and the cells adhered on the dish by settling for 19 to 24 hours. Preparation of the plasmid/lipofectin complex and incubation of cells with the complex were performed as described in the measurement of expression activity of luciferase. After the cells were incubated with the complex for a certain period, the medium containing the complex was removed and washed once with serum medium. Then fresh serum medium was added and localization of the fluorescence-labeled plasmid was observed using confocal laser scanning microscopy (TCS NT, manufactured by LAICA Co., Ltd.).

Figure 11:
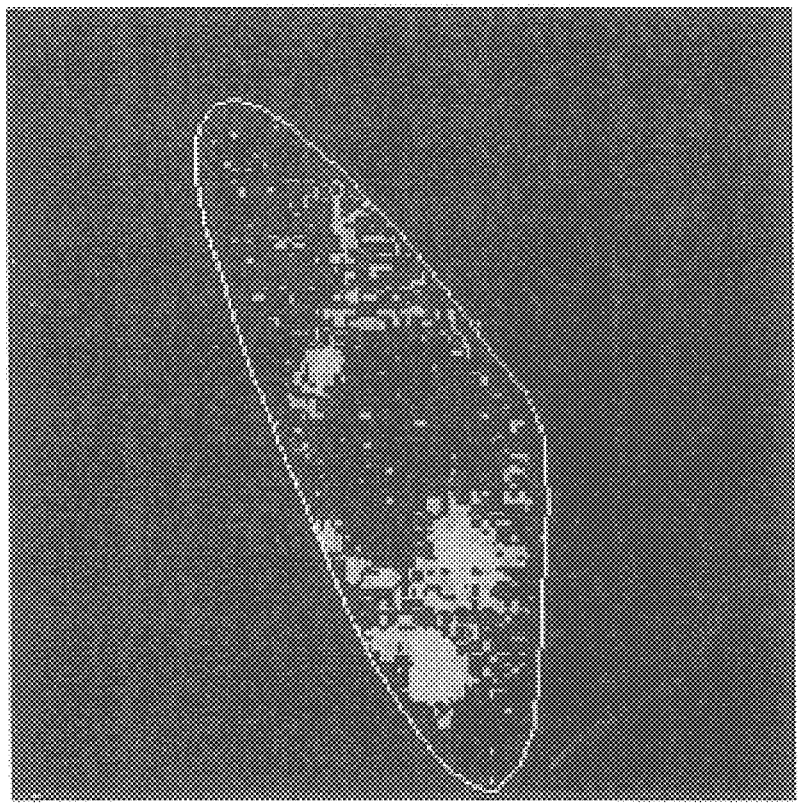
FIG. 11 is a photograph that shows a co-focusing image in which the localization of FITC-labeled plasmid is detected in HeLa cells.

The experiment was performed using HeLa cells. The results were shown in FIG. 11. Concerning control HeLa cells, incubated with fluorescence-labeled plasmid alone, fluorescence was not detected in the control cell. However, dots of fluorescence, indicating existence of labeled plasmid incorporated into the cells by the lipofectin, was observed in the cytoplasm of the cell. It is assumed that the plasmid was incorporated into the cell by the means of endocytosis when the plasmid/lipofectin complex was used. Therefore, the scattered fluorescence observed here seems to reflect localization of the complex incorporated by endocytosis. Thus the result of confocal laser scanning microscopy also indicates that fluorescent intensity of the fluorescence-labeled plasmid is sufficient for detection using confocal laser scanning microscopy.

What is claimed is:

1. A precursor compound of a fluorescence-labeled probe for a DNA, comprising:
   a residue of a fluorescence substance containing a hydrogen atom wherein said hydrogen atom is removed from said fluorescence substance;
   a conjugating group that binds to said residue;
   an alkylamino group having an alkyl group and amino group, said amino group being bonded to said conjugating group and said alkyl group being a linear or branched alkyl group having 1 to 16 carbon atoms; and
   a phenylamine having phenyl group and amino group, said alkyl group being bonded to said phenyl group at the para-position of said phenyl group, and said amino group being a primary amino group.

2. The precursor compound according to claim 1, wherein said fluorescence substance is selected from the group consisting of fluoroscein, sulforhodamine, rhodamine, dansyl chloride, and 7-chloro-4-nitrobenzoxyazole.

3. The precursor compound according to claim 1, wherein said conjugating group is selected from the group consisting of thioamide group, sulfonyl group and carbonyl group.

4. A fluorescence-labeled probe for a DNA, comprising:
   a residue of a fluorescence substance containing a hydrogen atom wherein said hydrogen atom is removed from said fluorescence substance;
   a conjugating group that binds to said residue;

an alkylamino group having an alkyl group and amino group, said amino group being bonded to said conjugating group and said alkyl group being a linear or branched alkyl group having 1 to 16 carbon atoms; and a phenyldiazonium group having phenyl group and diazonium group, said alkyl group being bonded to said phenyl group at the para-position of said phenyl group, and wherein said phenyl group is not substituted by a halogen atom.

5. The fluorescence-labeled probe according to claim 4, wherein said fluorescence substance is selected from the group consisting of fluoroscein, sulforhodamine, rhodamine, dansyl chloride and 7-chloro-4-nitrobenzoxyazole.

6. The fluorescence-labeled probe according to claim 4, wherein said conjugating group is selected from the group consisting of thioamide group, sulfonyl group and carbonyl group.

7. A fluorescence-labeled plasmid, comprising:

a residue of a fluorescence substance containing a hydrogen atom wherein said hydrogen atom is removed from said fluorescence substance;

a conjugating group that binds to said residue;

an alkylamino group having an alkyl group and amino group, said amino group being bonded to said conjugating group and said alkyl group being a linear or branched alkyl group having 1 to 16 carbon atoms;

a phenyldiazonium group having phenyl group and diazonium group, said alkyl group being bonded to said phenyl group at the para-position of said phenyl group, and wherein said phenyl group is not substituted by a halogen atom; and a plasmid composed of a DNA containing guanine, wherein said diazonium group binds to said plasmid through purine ring of said guanine.

8. The fluorescence-labeled plasmid according to claim 7, wherein said fluorescence substance is selected from the group consisting of fluoroscein, sulforhodamine, rhodamine, dansyl chloride, and 7-chloro-4-nitrobenzoxyazole.

9. The fluorescence-labeled plasmid according to claim 7, wherein said conjugating group is selected from the group consisting of thioamide group, sulfonyl group and carbonyl group.

10. A DNA stand labeled by said fluorescence-labeled probe according to claim 6.

11. A DNA sand labeled by said fluorescence-labeled probe according to claim 4.

12. A DNA stand labeled by said fluorescence-labeled probe according to claim 5.

* * * * *